United States Patent [19]

Yamanobe et al.

[11] Patent Number: 4,956,291

[45] Date of Patent: * Sep. 11, 1990

[54] METHOD FOR PRODUCTION OF CELLULOLYTIC ENZYMES AND METHOD FOR SACCHARIFICATION OF CELLULOSIC MATERIALS THEREWITH

[75] Inventors: Takashi Yamanobe; Yasushi Mitsuishi, both of Ibaraki; Yoshiyuki Takasaki, Chiba, all of Japan

[73] Assignees: Agency of Industrial Science & Technology; Ministry of International Trade & Industry, both of Tokyo, Japan

[*] Notice: The portion of the term of this patent subsequent to Dec. 31, 2002 has been disclaimed.

[21] Appl. No.: 11,043

[22] Filed: Feb. 5, 1987

Related U.S. Application Data

[63] Continuation of Ser. No. 720,416, Apr. 5, 1985, Pat. No. 4,742,005.

[30] Foreign Application Priority Data

Jan. 7, 1985 [JP] Japan ................................. 60-581
Jan. 11, 1985 [JP] Japan ................................. 60-3490

[51] Int. Cl.$^5$ .................. C12N 9/24; C12N 9/42; C12P 19/14
[52] U.S. Cl. .................. 435/200; 435/209; 435/99
[58] Field of Search .................. 435/99, 911, 200, 209

[56] References Cited

U.S. PATENT DOCUMENTS

| | | | |
|---|---|---|---|
| 4,144,354 | 3/1979 | Unno et al. | 426/2 |
| 4,562,150 | 12/1985 | Yamanobe et al. | 435/99 |
| 4,742,005 | 5/1988 | Yamanobe et al. | 435/99 |

Primary Examiner—John E. Tarcza
Attorney, Agent, or Firm—Oblon, Spivak, McClelland, Maier & Neustadt

[57] ABSTRACT

A method for the saccharification of a cellulosic material comprises the steps of culturing a microorganism of *Acremonium cellulolyticus* in a medium containing carbon sources and nitrogen sources, collecting a cellulolytic enzyme from the resultant culture broth, and causing the cellulolytic enzyme to act on the cellulosic material.

1 Claim, 1 Drawing Sheet

METHOD FOR PRODUCTION OF CELLULOLYTIC ENZYMES AND METHOD FOR SACCHARIFICATION OF CELLULOSIC MATERIALS THEREWITH

This is a continuation, of application Ser. No. 720,416, filed Apr. 5, 1985.

BACKGROUND OF THE INVENTION

1. Field of the Invention

This invention relates to a method for the production of cellulolytic enzymes by the use of a strain of genus *Acremonium cellulolyticus* and to a method for the saccharification of cellulosic materials by the use of the enzymes 2. Description of the prior art In recent years, the exploitation of reproductive plant biomass as a promising substitute for oil has been receiving earnest consideration. The plant biomass contains cellulosic materials composed preponderantly of cellulose and hemicellulose as principal polysaccharides. Glucose and pentose which are produced by the decomposition of such cellulosic materials are useful as food and feed and as important organic chemicals. Efforts are continued in search of effective methods for the saccharification of cellulosic materials. Particularly, the method for saccharification by the use of hydrolyzing enzymes is arresting keen interest.

Effective hydrolysis of cellulosic materials requires use of numerous enzymes possessing different substrate specificities because the cellulosic materials are composed of various components. Among all these enzymes, cellulase is the most important. The hydrolytic power the cellulase manifests on the cellulosic materials is enhanced when the cellulase is used in combination with a hemicellulose such as xylenase.

Cellulase is the generic term for a group of enzymes which catalyze an enzymatic reaction system for hydrolyzing cellulose into glucose, cellobiose, and celloolicomers. By the mode of activity, the enzymes of this group are divided into $C_1$ enzymes (specifically called Avicelase, cellobiohydrolase, FP-ase, and exo-$\beta$-glucanase), $C_x$ enzymes specifically called CMC-ase and endo-$\beta$-glucanase), $\beta$-glucosidase (otherwise called cellobiase), etc. The cellulase hydrolyzes cellulose eventually into glucose which is the constituent sugar of cellulose because a plurality of such enzymes manifest well-balanced interactions.

Xylanase is one type of hemicellulase. It selectively acts on xylan which is one of the hemicelluloses making up plant cell wall and hydrolyzes the xylan into its constituent monosaccharides such as xylose and xylooligomers which are polymers of xylose.

*Trichoderma reesei, Trichoderma viride,* and the microorganisms of Aspergillus genus, Penicillium genus, etc. have been widely studied for their ability to produce cellulolytic enzymes but they are not sufficiently productive of such enzymes. The cellulolytic enzymes they produce are deficient in hydrolytic power and thermal stability and, therefore, are incapable of thoroughly hydrolyzing cellulosic materials. The hydrolysates obtained by these cellulolytic enzymes have cellobiose and other oligomers contained therein in large amounts.

The inventors have screened a host of microorganisms occurring widely in nature in search of a cellulolytic enzyme possessing high ability to hydrolyze crystalline cellulose and saccharify the cellulose into glucose. They have found that the cellulolytic enzymes produced by a mold isolated from soil and identified to be *Acremonium cellulolyticus* (FERM BP-495) include a cellulase which exhibits a strong hydrolytic power to crystalline cellulose and possesses a notably strong $\beta$-glucosidase activity and, therefore, enjoys extremely high ability to saccharify cellulose substantially completely into glucose. These cellulolytic enzymes further include a xylanse which excels in thermostability and exhibits high ability to saccharify xylan.

The main object of this invention is to provide a method for the production of cellulolytic enzymes including a cellulase capable of hydrolyzing cellulose substantially completely into glucose and a thermostable xylanase and a method for enhancing the production of the enzymes.

SUMMARY OF THE INVENTION

To accomplish the object described above, the method of this invention comprises the steps of culturing a Tolnaftate-resistant strain of *Acremonium cellulolyticus* in a culture medium containing carbon sources and nitrogen sources and collecting from the resultant culture broth cellulolytic enzymes containing cellulase and thermostable xylanase activity in conspicuous amounts.

When the aforementioned Acremonium *cellulolyticus* is caused to acquire resistance to Tolnaftate (m,N-Dimethyl thiocarbanilic acid O-2-naphthyl ester), it is improved in its cellulolytic enzyme-producing ability and consequently enabled to produce cellulase and xylanase in remarkably increased amounts. By culturing the aforementioned strain in a culture medium containing xylan, the yield of a thermostable xylanase can be selectively enhanced.

When cellulolytic enzymes containing both xylanase and cellulase are used in the hydrolysis of a cellulosic substance such as rice straw, bagasse, or forage which contains cellulose and hemicelluloses formed mainly of xylan, the hemicelluloses are decomposed and removed by the xylanase and consequently the hydrolysis of the cellulose is effected with enhanced efficiency. In this manner, the raw material containing hemicelluloses can be hydrolyzed thoroughly.

BRIEF EXPLANATION OF THE DRAWING

FIG. 1(*b*) is a graph showing the optimum temperature data of the xylanase of the present invention.

FIG. 2(*b*) is a graph showing thermostability of the xylanase of the present invention

DESCRIPTION OF PREFERRED EMBODIMENT

Figure 1A:
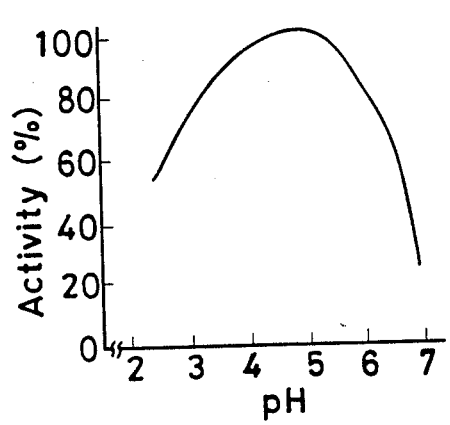
FIG. 1(*a*) is a graph showing the optimum pH data obtained of the thermostable xylanase of the present invention.

First, the method for fortifying the resistance to Tolnaftate of the wild strain of *Acremonium cellulolyticus* (FERM BP-495) will be described.

*Acremonium cellulolyticus* (FERM BP-495) is suspended in a Czapek medium (containing 0.3% of $NaNO_3$, 0.1% of $K_2HPO_4$, $5\times10^{-2}$% of $MgSO_4\times7$-$H_2O$, $5\times10^{-2}$% of KCl, $1\times10^{-2}$% $FeSO_4\times7H_2O$, and 1% of glucose). The suspension, with nitrosoguanidine (N-methyl-N'-nitro-N-nitrosoguanidine) added thereto in a concentration of up to $3\times10^{-2}$%, is incubated at room temperature for 0.5 to 3 hours. The culture broth consequently obtained is centrifuged to recover cells The cells are thoroughly washed with a Czapek medium and then suspended in the same medium. Part of the suspension is spread on a Czapek agar medium (containing 0.3% of $NaNO_3$, 0.1% of $K_2HPO_4$, $5\times10^{-2}$% of $MgSO_4\times 7H_2O$, $5\times10^{-2}$% of KCl, $1\times10^{-3}$% of $FeSO_4\times 7H_2O$, 1% of glucose 1.5% of agar, $2.5\times10^{-2}$% of Streptomycin, and $2.5\times10^{-2}$% of penicillin G, and having pH 5.6) additionally incorporating $4\times10^{-2}$ to $2\times10^{-5}$% of Tolnaftate and incubated at 30° C. The Tolnaftate-resistant mutant which grows is transferred onto a slant medium of the same composition and preserved thereon. In the Tolnaftate-resistant mutant thus obtained, a strain of enhanced cellulase-producing ability is recognized in high frequency. The suspensions of the cells of wild type and resistant mutant are spread on Czapek agar media containing $4\times10^{-2}$ to $1\times10^{-2}$% of Tolnaftate and cultured at 30° C. During the culture, the resistant mutant shows comparatively satisfactory growth and the wild type shows absolutely no growth.

The present strain differs from *Acremonium cellulolyticus*, the parent, in respect that it possesses resistance to Tolnaftate and exhibits high glycanase activity. Thus, it is recognized to be a novel mutant of *Acremonium cellulolyticus*. Since this mutant simultaneously produces xylanase and cellulase similarly to its parent, it has been named Acremonium cellulolyticus TN.

This strain was deposited at Fermentation Research Institute, Agency of Industrial Science & Technology, Ministry of International Trade & Industry, on Oct. 13, 1984, under FERM P-7894 and was also deposited at the same Institute in compliance with the Budapest Treaty on the same day and designated FERM BP-685.

Data comparing the amounts of cellulolytic enzymes produced by the parent strain and the TN strain of *Acremonium cellulolyticus* are shown by way of one example in Table 1.

TABLE 1

| Microorganism used | Amount of enzyme produced (units/ml of medium) | | | |
|---|---|---|---|---|
| | Avicelase | CMC-ase | β-Glucosidase | Xylanase |
| Parent strain | 5.7 | 69.1 | 30.9 | 5.2 |
| TN strain | 15.0 | 167 | 59.4 | 12.3 |

It is noted from the table that the amounts of cellulolytic enzymes produced by the Tolnaftate-resistant mutant are about three times (Avicelase and CMC-ase) and about two times (β-glucosidase and xylanase) those produced by the parent strain. The enzymes so produced exhibit notably enhanced hydrolytic ability. No case where a resistant mutant of a microorganism has been produced with the resistance to Tolnaftate as a marker to enhance the yield of cellulase and other enzymes produced by the microorganism is found in the literature prior to this invention.

The mycological properties of the TN strain will be shown below. The mycological properties of the parent strain are not shown since they are substantially the same as those of *Acremonium cellulolyticus* TN.

Growth: On malt extract agar, growth proceeds rapidly to reach a diameter of 70 mm in seven days at 30° C. Colonies are white at first and assume a slightly yellowish color afterward. Aerial hyphae slowly rise and assume a floccose appearance and occasionally form a ropy aggregate of hyphae. In the latter stage of culture, the rear sides of colonies assume a rosy brown to reddish brown color. Substantially similar growth proceeds on Czapek agar, though with smaller rise of aerial hyphae. The pH range for growth is 3.5 to 6.0, with the optimum pH falling near 4. The temperature range for growth is 15° C. to 43° C., with the optimum growth temperature falling near 30° C.

Morphology: Hyphae measure 0.5 to 2.5 μm in diameter, are colorless and contain septum. They have a smooth surface.

Conidia: Conidium-forming ability is extremely instable. Conidia readily disappear during sub-culture on Czapek agar and on malt extract agar medium. During isolation, conidiophores are observed to protrude from lateral sides of aerial hypha and are colorless. Conidia are in the shape of semi-spheres (2.5~5×2~4.5 μm) of smooth surface and are devoid of color. They are chained very loosely and are liable to disperse.

For the production of cellulase and/or xylanase by the strain of genus Acremonium, this strain is required to be aerobically cultured at temperatures of about 20° to 40° C. for a period of about 2 to 15 days in a liquid or solid medium generally containing, as a carbon source, cellulose or a cellulosic material such as Avicel, xyloglucan, cotton, bagasse, or wheat bran and as a nitrogen source, an organic or inorganic nitrogen-containing substance such as a nitrate, ammonium salt, urea, peptone, or yeast extract, and a small amount of a metal salt.

Addition of betaine in a proportion of 0.01 to 1% to the foregoing medium brings about an increase by 10 to 50% of the produced amounts of cellulases, particularly carboxymethylcellulase, β-glucosidase, and xylanase.

Addition of lecithin in a proportion of 0.1 to 1%, similarly to the addition of betaine, enhances the produced amounts of cellulases, particularly carboxymethylcellulase and β-glucosidase, by 20 to 30%. The lecithin to be used effectively for this purpose may be a product originating in animals or plants or a product of synthesis. Lecithin of soybean origin is available at a low price.

Since the cellulase and/or xylanase are extracellular enzymes, they can be finally collected in the form of supernatant obtained by filtration of the culture broth in the case of liquid culture or in the form of enzyme solution obtained by extracting the culture solid with water or some other suitable inorganic salt solution in the case of solid culture. The enzyme so collected is finished in a powdered form by lyophilization.

As regards xylanase alone, since the enzyme is thermostable, it may be treated at pH 4.9 at 65° C. for two hours to remove the coexisting cellulase through convertive precipitation without impairing the activity of xylanase. Consequently, an enzyme solution which has only xylanase activity can be prepared easily.

Now, the enzymatic properties of Avicelase, CMC-ase and β-glucosidase will be described below.

(A) ENZYMATIC PROPERTIES OF AVICELASE (1) Activity

Enzymes act directly on insoluble crystalline cellulose such as cellulose powder, Avicel and absorbent cotton and produce reducing sugars such as glucose and cellobiose.

(2) Working pH and optimum pH

The working pH of this enzyme is found to fall in the range of 2 to 8 and the optimum pH thereof to fall near 4.5.

(3) pH stability

The pH at which the enzyme, when left standing in the citrate-phosphate buffer at 45° C. for 20 hours, manifests stability is found to fall in the range of about 3.5 to about 5.5.

(4) Range of working temperature and optimum temperature

The enzyme shows its activity intact at elevated temperatures up to about 90° C. This enzyme, when allowed to react with 1% Avicel in the presence of 0.05M acetate buffer (pH 4.5) for 10 minutes, is found to have its optimum working temperature near 65° C.

(5) Thermal stability

When the enzyme is heated in 0.05M acetate buffer (pH 4.5) for 10 minutes, it undergoes substantially no inactivation at temperatures up to about 60° C. It is inactivated to about 50% and about 80% respectively after 10 minutes' heating at 65° C. and 70° C.

(6) Inhibitors

This enzyme is strongly inhibited by mercury ions and copper ions among other various metallic ions. It is also inhibited to about 80% by p-chloro-mercutic benzoate, an SH inhibitor, at a concentration of 1 mM.

(7) Method of purification

This enzyme can be purified by desalting and concentrating the culture filtrate with hollow fibers (Amicon HI-P5), separating the concentrated filtrate by column chromatography (NaCl O→1M gradient) using DEAE-Sepharose (CL-6B), and treating the separated filtrate again by the same column chromatography (NaCl O→0.6M gradient) system.

(8) Molecular weight

The molecular weight of this enzyme, when determined by the gel filtration method using a Bio-gel (A 0.5 m) column, is about 60,000.

(9) Method for determination of activity

The activity of this enzyme is determined by combining 0.5 ml of a suspension (pH 4.5) containing Avicel in a concentration of 0.5% in 0.1M acetate buffer with a suitable amount of the enzyme solution, diluting the resultant mixture with distilled water to a total volume of 1.0 ml, heating the mixed solution at 50° C. to induce reaction of the enzyme upon Avicel, and measuring the amount of reducing sugar formed by the reaction according to the Somogyi-Nelson method The amount of the enzyme which generates reducing power equivalent to 1$\mu$mole of glucose per minute is taken as 1 unit.

(B) ENZYMATIC PROPERTIES OF CMC-ASE

(1) Multiple forms of CMC-ase

By means of the disc gel electrophoresis, the CMC-ase is divided into at least four components, which are mutually discriminable by molecular weight and isoelectric point The CMC-ase I has a molecular weight of about 160,000 and an isoelectric point of 5.08, II about 160,000 and 4.95, III about 120,000 and 4.60, and IV about 120,000 and 4.48 respectively Thus, the CMC-ase is formed of a complex of such isozymes (2) This enzyme consists of components (CMC-ase I and II) which act upon such soluble cellulose derivatives as carboxymethyl cellulose (CMC) and hydrolyze them into glucose and cellobiose and components (CMC-ase III and IV) which produce glucose only minimally and hydrolyze cellulose into cellooligo-saccharides of the minimum level of cellobiose

(3) Working pH and optimum pH

The working pH of the CMC-ase complex is found to cover a wide range of 2 to 8 and the optimum pH thereof is found to be about 4.5.

(4) pH stability

The pH at which the CMC-ase complex, when left standing in the citrate-phosphate buffer at 45° C. for 20 hours, manifests stability is found to fall in the range of about 3.5 to about 6.

(5) Range of working temperature and optimum temperature

This CMC-ase complex shows its activity intact at elevated temperatures up to about 90° C. This complex, when allowed to react with 1% CMC in the presence of 0.05M acetate buffer (pH 4.5) for 10 minutes, is recognized to have its optimum working temperature near 60° C.

(6) Thermal stability

When this enzyme is heated in 0.05M acetate buffer (pH 4.5) for 10 minutes, it undergoes substantially no inactivation at temperatures up to about 60° C. It is inactivated to about 40% and about 70% respectively after 10 minutes' heating at 65° C. and 70° C.

(7) Inhibitors

This enzyme is strongly inhibited by mercury ions and copper ions both of concentrations of at least 1 mM among various other metallic ions.

(8) Method of purification

This enzyme can be purified and isolated into the component isozymes by desalting and concentrating the culture filtrate with hollow fibers (Amicon HI-P5), then separating the concentrated filtrate by column chromatography (NaCl O→1.0M gradient) using DEAESepharose (CL-6B), and treating the separated filtrate by the same column chromatography system.

(9) Method for determination of activity

The activity of this enzyme is determined by combining 0.5 ml of a solution (pH 4.5) containing 1% CMC in 0.1M acetate buffer with a suitable amount of enzyme solution, diluting the resultant mixture with distilled water to a total volume of 1.0 ml, heating the diluted solution at 50° C. to induce reaction of the enzyme upon the CMC, and measuring the amount of produced reducing sugar by the Somogyi-Nelson method.

The amount of the enzyme which generates reducing power equivalent to 1 $\mu$mole of glucose per minute is taken as 1 unit.

(C) Enzymatic properties of β-glucosidase

(1) Activity

The β-glucosidase acts on cellooligosaccharides such as salicin, cellobiose, cellotriose, cellotetraose, cellopentaose and cellohexaose and hydrolyzes them into glucose. It also acts on high-molecular celluloses such as Avicel but shows virtually no activity on CMC and HEC (hydroxyethyl cellulose). The Km values of this enzyme relative to salicin, cellobiose, cellotriose, cellotetraose, cellopentaose, and cellohexaose are 3.40, 2.26, 1.19, 0.82, 0.52, and 0.51 mM.

(2) Working pH and optimum pH

The working pH of this enzyme is found to fall in the range of 2 to 8 and the optimum pH thereof to fall near 4.5.

(3) pH stability

The pH at which the enzyme, when left standing in the citrate-phosphate buffer at 45° C. for 20 hours, manifests stability is found to fall in the range of about 3.5 to about 5.

(4) Range of working temperature and optimum temperature

The enzyme shows its activity intact at elevated temperatures up to about 90° C. This enzyme, when allowed to react with 1% salicin in the presence of 0.05M acetate buffer (pH 4.5) for 10 minutes, is recognized to have its optimum working temperature near 70° C.

(5) Thermal stability

When this enzyme is heated in 0.05M acetate buffer (pH 4.5) for 10 minutes, it undergoes substantially no inactivation at temperatures up to about 60° C. It is inactivated to about 40% and to about 90% or more respectively after 10 minutes' heating at 70° C. and 80° C.

(6) Inhibitors

This enzyme is strongly inhibited by mercury ions and copper ions. Further glucono-6-lactone acts as an antagonistic inhibitor on the substrate.

(7) Method of purification

This enzyme can be purified to the degree of electrophoretic homogeneity by desalting and concentrating the culture filtrate with hollow fibers (Amicon HI-P5), separating the concentrated filtrate by column chromatography (NaCl 0→1M gradient) using DEAE-Sepharose (CL-6B), and subjecting the active fraction to chromato-focusing (pH 6→4) and to gel filtration with Bio-gel (A 0.5 m).

(8) Molecular weight

The molecular weight of this enzyme, when determined by the gel filtration method using a Bio-gel (A 0.5 m) column, is about 240,000.

(9) Method for determination of activity

The activity of this enzyme is determined by combining 0.5 ml of a solution (pH 4.5) containing salicin in a concentration of 1% in 0.1M acetate buffer with a suitable amount of the enzyme solution, diluting the resultant mixture with distilled water to a total volume of 1.0 ml, heating the reaction mixture at 50° C. to induce reaction of the enzyme upon salicin, and measuring the amount of the produced reducing sugar by the Somogyi-Nelson method.

The amount of the enzyme which generates reducing power equivalent to 1 μmole of glucose per minute is taken as 1 unit.

The enzymatic properties of xylanase produced by the present invention will be described below.

(1) Multiple forms of xylanase

By means of the disc gel electrophoresis, the xylanase is divided into at least three components, which are mutually discriminable by molecular weight and isoelectric point. The xylanase A has a molecular weight of about 51,000 and an isoelectric point of 5.05, xylanase B about 46,000 and 4.57 and xylanase C about 36,000 and 3.55 respectively. Thus, the xylanase is formed of a complex of such components.

(2) Action

Xylanase complex acts upon soluble and insoluble xylan contained in plant biomass and produces xylose and xylooligosaccharides. When xylanase complex acts upon arabinoxylan containing arabinose, arabinose and oligosaccharides comprising arabinose and xylose are produced beside xylose and xylooligosaccharides. Also, the present complex acts effectively upon xylobiose and hydrolyzes it into xylose. Accordingly, final products comprise mainly xylose.

(3) Working pH and optimum pH

The working pH of the xylanase complex is found to cover a range of 3 to 6 as shown in FIG. 1(a) and the optimum pH thereof is found to be about 5.

(4) pH stability

Figure 2A:
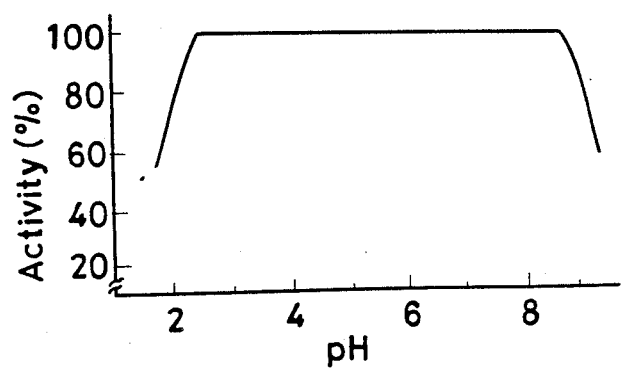
FIG. 2(*a*) is a graph showing the pH stability of the xylanase of the present invention.

The pH at which the xylanase complex, when left standing in the citrate-phosphate buffer at 25° C. for 24 hours, manifests stability is found to fall in the range of about 2.5 to about 8.5 as shown in FIG. 2(a).

(5) Range of working temperature and optimum temperature

Figure 1B:
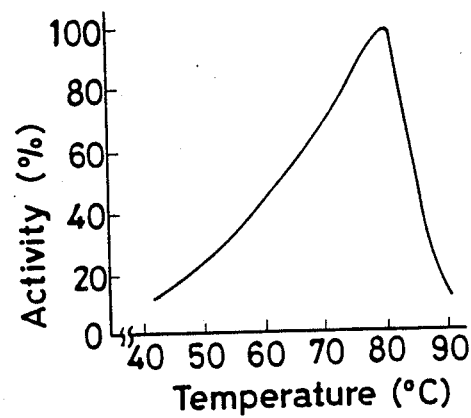

This xylanase complex shows its activity intact at elevated temperatures up to about 90° C. This complex, when allowed to act upon 0.25% xylan in the presence of 0.05M acetate buffer (pH 4.9) for 10 minutes, is recognized to have its optimum temperature about 80° C. as shown in FIG. 1(b).

(6) Thermal stability

Figure 2B:
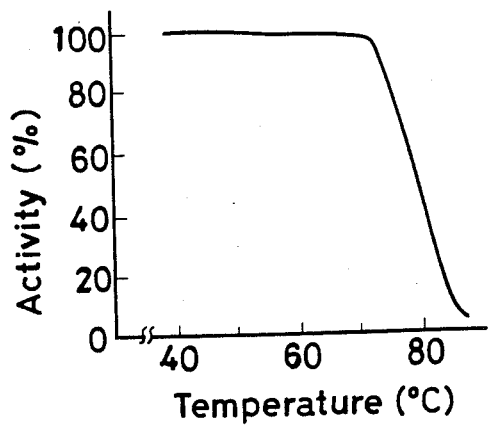

When this complex is heated in 0.1M acetate buffer (pH 4.9) for 10 minutes, it undergoes substantially no inactivation at temperatures up to about 70° C. as shown in FIG. 2(b). It is inactivated to about 60% and about 90% respectively after 10 minutes' heating at 80° C. and 85° C.

(7) Inhibitors

This complex is strongly inhibited by mercury ions and silver ions both of concentrations of at least 1 mM among other various metallic ions.

(8) Method of purification

This xylanase complex can be purified to the degree of electrophoretic homogeneity and isolated into three components by heating the culture filtrate at 65° C. for two hours to modify the impure protein contained in the culture filtrate into a precipitate, removing the precipitate from the culture filtrate by centrifugal separation, and analyzing the resultant culture filtrate by the use of column chromatography using DEAE-Sepharose and chromato-focusing.

(9) Method for determination of activity

The activity of this xylanase complex is determined by adding 0.5 ml of a substrate solution (pH 4.5) containing 0.5% xylan (containing about 9% arabinose) prepared from rice straw with 0.1M acetate buffer to a suitable amount of complex, diluting the resultant mixture with distilled water to a total volume of 1.0 ml, incubating the reaction mixture at 60° C. for 10 minutes, and measuring the amount of produced reducing sugar by the Somogyi-Nelson method.

The amount of the xylanase complex which generates reducing power equivalent to 1 μmole of xylose per minute is taken as 1 unit.

The reaction for hydrolyzing a cellulosic material by the use of a cellulase preparation offered by the present invention is generally carried out at pH 3–7, preferably at 4–5, at a temperature in the range of 30° to 65° C. Examples of the substrate usable for this purpose include not only pure celluloses such as powdered cellulose, cotton, and Avicel but also cellulose-containing substances such as bagasse, Napier grass, rice straw, wheat straw, and rice hull. Prior to saccharification, such cellulosic substances of plant origin are subjected to a pretreatment such as an alkali treatment, crushing, or irradiation. The substrate concentration is desired to be as high as permissible. Generally, the substrate is used in the range of 5 to 30%.

The amount of the cellulase preparation required to be added to the cellulosic substance is on the order of 20 units/g as Avicelase. The cellulase preparation so added is effective enough to hydrolyze more than 80% of cellulose substantially completely into glucose.

The xylanase which is contained in the cellulase preparation produced by the TN strain has its optimum working temperature in a high temperature range and possesses high ability to saccharify xylan. When the preparation is used on a cellulosic material, therefore, the xylanase acts on xylan present in the material and saccharifies it into xylose. This preparation, used in animal feed, serves to improve the edibility of the feed. When it is used in coffee beans, it serves to promote the extraction of coffee essence. The preparation is effective further in the respect that since the xylanase component thereof hydrolyzes the matrix of hemicellulose enveloping the cellulose, the cullulase component thereof is allowed to enjoy easy access to the cellulose and heighten the hydrolysis of cellulose.

Now, the present invention will be described more specifically below with reference to examples. This invention is not limited to these examples.

EXAMPLE 1

In an Erlenmeyer flask having an inner volume of 200 ml, 20 ml of a culture medium (pH 4.0) containing 4% of cellulose, 1% of Bacto-peptone, 0.6% of potassium nitrate, 0.2% of urea, 0.16% of potassium chloride, 0.12% of magnesium sulfate, 1.2% of potassium secondary phosphate, $1\times10^{-3}$% of zinc sulfate, $1\times10^{-3}$% of manganese sulfate, and $1\times10^{-3}$% of copper sulfate was placed and sterilized by an ordinary method. In the sterilized culture medium, a strain of *Acremonium cellulqlyticus* TN (FERM BP-685) inoculated thereto was aerobically cultured at 30° C. for ten days. At the end of the culture, the culture broth was centrifuged to precipitate cells. The supernatant consequently obtained was tested for Avicelase activity, CMC-ase activity, β-glucosidase activity and xylanase activity For comparison, the parent strain, i.e. *Acremonium cellulolyticus* (FERM BP-495), was cultured on a medium of the same composition under the same conditions as described above The enzyme produced in consequence of the culture was tested for activity. The results are shown in Table 2.

TABLE 2

| Microorganism used | Amount of enzyme produced (units/ml of medium) | | | |
|---|---|---|---|---|
| | Avicelase | CMC-ase | β-Glucosidase | Xylanase |
| Parent strain | 7.7 | 65.1 | 23.7 | 8.2 |
| TN strain | 14.8 | 158.3 | 46.4 | 19.1 |

It is noted from the table that the amounts of enzymes produced by the Tolnaftate-resistant mutant (TN strain) are about three times in CMC-ase and about two times in Avicelase, β-glucosidase, and xylanase, those produced by the parent strain.

EXAMPLE 2

A medium having betaine added in a proportion of 0.03% to the medium of Example 1 and a medium having lecithin of soybean origin added in a proportion of 0.5% to the medium of Example 1 were prepared. On these media, *Acremonium cellulolyticus* TN (FERM BP-685) was aerobically cultured at 30° C. for 12 days. The resultant culture broths were centrifuged. The produced cellulases in the supernatants were tested for Avicelase activity, CMC-ase activity, β-glucosidase activity and xylanase activity. The results are shown in Table 3.

TABLE 3

| | Avicelase (units/ml) | CMC-ase (units/ml) | β-Glucosidase (units/ml) | Xylanase (units/ml) |
|---|---|---|---|---|
| Control | 12.7 | 167 | 59.4 | 20.1 |
| Betaine contained | 16.2 | 251 | 88.1 | 27.6 |
| Lecithin contained | 14.8 | 305 | 94.3 | 22.5 |

It is noted from the table that addition of betaine or lecithin permits Avicelase, CMC-ase, β-glucosidase and xylanase to be produced in amounts increased from the levels obtained in the absence of this addition and that this effect is particularly conspicuous in the production of CMC-ase and βglucosidase.

EXAMPLE 3

A cellulosic substance (produced by Sanyo-Kokusaku Pulp Co., Ltd., Japan and marketed under tradename "KC Flok, W-100") was tried for saccharification.

The cellulase prepared by the procedure of Example 1 was added in varying amounts, 15, 30, and 60 units as Avicelase, each to 3-g portions of KC Flok. The specimens thus prepared were diluted with added water to a total volume of 15 ml and left reacting at 50° C., with the pH value kept about 5. At the 95th hour of the reaction, portions of the saccharified solutions were separated and analyzed for reducing sugar content by the Somogyi-Nelson method and for total sugar by Anthrone method. The results are shown in Table 4.

TABLE 4

| Amount of enzyme used (units/g) | Reducing sugar (mg/ml) | Total sugar (mg/ml) | Ratio of saccharification (%) |
|---|---|---|---|
| 5 | 142 | 191 | 74.3 |
| 10 | 162 | 199 | 81.4 |
| 20 | 178 | 199 | 89.4 |

Ratio of saccharification: (Reducing sugar)/(total sugar) × 100

EXAMPLE 4

As a cellulosic substance, a product of James River Co., Berlin marketed under tradename "Solka Flok, BW-200" was adopted.

The cellulase prepared by the procedure of Example 1 was added in an amount of 40 units/g of substrate to Solka Flok used in different amounts of 0.5 g and 1 g. The specimens thus prepared were diluted to a total volume of 10 ml and subjected to saccharification at 50° C. for 48 hours, with the pH value at 4.5. The sacchari-fied solutions were analyzed for reducing sugar and glucose contents. The results are shown in Table 5.

TABLE 5

| Concentration of Solka Flok (%) | Reducing sugar (mg/ml) | Ratio of saccharification (%) | Glucose (mg/ml) | Glucose content (%) |
|---|---|---|---|---|
| 5 | 41.6 | 86.4 | 37.5 | 90.6 |
| 10 | 80.0 | 82.6 | 67.5 | 84.3 |

Glucose content: (Glucose)/(reducing sugar) × 100

EXAMPLE 5

An alkali swelling cellulose (prepared by keeping powdered cellulose immersed in an aqueous 17.5% NaOH solution at 25° C. for four hours and washing the impregnated cellulose with water) was suspended as a cellulosic substance in a reaction solution in final concentrations of 9.0, 18.0, and 27.0%. The cellulase prepared by the procedure of Example 1 was added in a fixed ratio of 5 units/g of substrate as Avicelase to the suspensions. The specimens thus prepared were diluted to a total volume of 5 ml and subjected to saccharification at 50° C. for 72 hours, with the pH value at 4.5. The resultant saccharified solutions were analyzed for reducing sugar and total sugar contents. The results are shown in Table 6.

TABLE 6

| Concentration of alkali swelling cellulose (%) | Reducing sugar (mg/ml) | Total sugar (mg/ml) | Ratio of saccharification (%) |
|---|---|---|---|
| 9.0 | 86 | 87 | 98.9 |
| 18.0 | 170 | 173 | 98.3 |
| 27.0 | 241 | 260 | 92.7 |

EXAMPLE 6

Napier grass delignified with peracetic acid was suspended as a cellulosic substance in a reaction solution in final concentrations of 2, 5, and 7%. The cellulase prepared by the procedure of Example 1 was added in a fixed ratio of 20 units/g of substrate as Avicelase. The specimens thus prepared were diluted to a total volume of 5 ml and subjected to saccharification at 50° C. for 24 hours, with the pH value at 4.5. The resultant saccharified solutions were analyzed for reducing sugar and total sugar contents. The results are shown in Table 7.

TABLE 7

| Concentration of delignified napier grass (%) | Reducing sugar (mg/ml) | Total sugar (mg/ml) | Ratio of saccharification (%) | Neutral sugar (%) | | |
|---|---|---|---|---|---|---|
| | | | | Arabinose | Xylose | Glucose |
| 2 | 17 | 22 | 78 | 5.6 | 24.2 | 69.0 |
| 5 | 39 | 54 | 72 | 6.1 | 22.2 | 68.3 |
| 7 | 45 | 75 | 60 | 5.1 | 12.5 | 80.4 |

EXAMPLE 7

In an Erlenmeyer flask having an inner volume of 200 ml, 20 ml of a medium containing 4% of cellulose, 1% of peptone, 0.6% of potassium sulfate, 0.16% of potassium chloride, 0.16% of sodium chloride, 0.12% of magnesium sulfate, 1.20% of potassium phosphate, and 0.001% each of zinc sulfate, manganese sulfate, and copper sulfate (pH 4.0) was sterilized by an ordinary method, inoculated with *Acremonium cellulolyticus* TN (FERM BP-685), and left standing at 30° C. for six days to effect aerobic culture. The resultant culture broth was centrifuged to separate the cells. The supernatant was tested for xylanase activity. The activity was found to be 15.2 units/ml of the broth. The culture broth was found to contain 167 units of cellulase as CMC-ase.

EXAMPLE 8

The procedure of Example 7 was followed, except that 2% of xyloglucan (product of Dainippon Pharmaceutical Co., Ltd., Japan, marketed under tradename "Glyloid 3S") was used in place of cellulose and the aerobic culture was continued for eight days. The resultant culture broth was centrifuged. The supernatant was analyzed for xylanase activity. This activity was found to be 26.4 units/ml of the culture broth. The culture broth was found to contain 120 units of cellulase as CMC-ase.

The supernatant was adjusted to pH 4.9 and heated at 65° C. for two hours. The precipitate which occured during the treatment was removed by centrifugation. Consequently, there was obtained an enzyme as a standard substance. The recovery ratio of xylanase was calculated to be 92.4%.

EXAMPLE 9

The standard enzyme obtained in Example 8 was added in a final concentration of 20 units/ml to an aqueous 10% xylanase solution and subjected to saccharification at 65° C. for 48 hours. Part of the resultant saccharified solution was analyzed for reducing sugar content. The reducing sugar content was found to be 60 mg/ml as xylose. This value corresponds to 88.2% of the value (68 mg/ml) obtained by hydrolyzing xylan of the same concentration with sulfuric acid. When the hydrolyzate was analyzed by paper partition chromatography, it was found to be composed preponderantly of xylose and accompanied by a very small proportion of xylobiose.

What is claimed is:

1. A method for production of a cellulose/xylanase enzyme composite, which comprises: culturing *Acremonium celluloyticus* BP-495 in a culture medium containing carbon and nitrogen sources and collecting said enzyme composite from the resultant culture broth.

* * * * *